(12) United States Patent
Madden et al.

(10) Patent No.: US 11,253,386 B2
(45) Date of Patent: *Feb. 22, 2022

(54) RIGID ANKLE SUPPORT SYSTEM

(71) Applicant: DJO, LLC, Vista, CA (US)

(72) Inventors: David Madden, Forest Lake, MN (US); Matthew Cozad, Minneapolis, MN (US); Brian Bowen, Lakeville, MN (US); Frank Ledezma, Brookfield, WI (US)

(73) Assignee: DJO, LLC, Carlsbad, CA (US)

( * ) Notice: Subject to any disclaimer, the term of this patent is extended or adjusted under 35 U.S.C. 154(b) by 525 days.

This patent is subject to a terminal disclaimer.

(21) Appl. No.: 16/153,553

(22) Filed: Oct. 5, 2018

(65) Prior Publication Data

US 2019/0070032 A1   Mar. 7, 2019

Related U.S. Application Data

(63) Continuation of application No. 14/612,136, filed on Feb. 2, 2015, now Pat. No. 10,092,439.

(Continued)

(51) Int. Cl.
*A61F 5/01* (2006.01)

(52) U.S. Cl.
CPC .... *A61F 5/0127* (2013.01); *A61F 2210/0071* (2013.01); *A61F 2210/0076* (2013.01)

(58) Field of Classification Search
CPC .... A61F 5/0111; A61F 5/0127; A61F 13/066; A61F 5/0585; A61F 13/04; A61F 5/0118;
(Continued)

(56) References Cited

U.S. PATENT DOCUMENTS 4,771,768 A    9/1988  Crispin
4,888,225 A   12/1989  Sandvig et al.
(Continued)

FOREIGN PATENT DOCUMENTS

WO    WO 10/099130    9/2010

OTHER PUBLICATIONS

International Search Report and Written Opinion dated Apr. 29, 2015 in PCT/US15/014142.
(Continued)

*Primary Examiner* — Ophelia A Hawthorne
(74) *Attorney, Agent, or Firm* — Knobbe, Martens, Olson & Bear LLP

(57) ABSTRACT

A moldable rigid ankle brace is disclosed. The rigid stabilizing ankle brace includes a heat-moldable multi-layer housing having an opening for receiving a user's ankle, a footplate attached to the housing, and a closure mechanism. The multi-layer housing includes a middle layer, which is substantially stiff at a temperature below about 130° F. and moldable at temperatures between about 130° F. and 275° F. A method of stabilizing an ankle is also disclosed. The method may include providing a rigid stabilizing ankle brace, having a heat-moldable multi-layer housing having an opening for receiving a user's ankle, and a footplate removably attached to said housing, heating the ankle brace to between about 130° F. to about 275° F., and applying said heated ankle brace to the ankle of a patient in need thereof.

19 Claims, 6 Drawing Sheets

Related U.S. Application Data

(60) Provisional application No. 61/935,756, filed on Feb. 4, 2014, provisional application No. 61/935,755, filed on Feb. 4, 2014.

(58) Field of Classification Search
CPC .............. A61F 5/01; A61F 2210/0071; A61F 2210/0076; A43B 7/20; A61L 15/07; A61L 15/12
See application file for complete search history.

(56) References Cited

U.S. PATENT DOCUMENTS

| | | | |
|---|---|---|---|
| 4,934,355 A | 6/1990 | Porcelli | |
| 5,069,202 A | 12/1991 | Prock | |
| 5,176,623 A | 1/1993 | Stetman et al. | |
| 5,429,588 A | 7/1995 | Young et al. | |
| 5,720,715 A | 2/1998 | Eriksson | |
| 5,934,599 A | 8/1999 | Hammerslag | |
| 5,971,946 A | 10/1999 | Quinn et al. | |
| 6,053,884 A | 4/2000 | Peters | |
| 6,202,953 B1 | 3/2001 | Hammerslag | |
| 6,289,558 B1 | 9/2001 | Hammerslag | |
| 6,767,332 B1 | 7/2004 | Pardue et al. | |
| 7,785,283 B1 | 8/2010 | Bledsoe | |
| 8,048,012 B1 * | 11/2011 | Castro | A61F 5/0127 602/23 |
| 10,004,627 B2 | 6/2018 | Madden et al. | |
| 10,092,439 B2 * | 10/2018 | Madden | A61F 5/0127 |
| 2002/0095750 A1 | 7/2002 | Hammerslag | |
| 2003/0204938 A1 | 11/2003 | Hammerslag | |
| 2005/0085755 A1 | 4/2005 | Rabe | |
| 2006/0156517 A1 | 7/2006 | Hammerslag | |
| 2008/0060167 A1 | 3/2008 | Hammerslag | |
| 2008/0060168 A1 | 3/2008 | Hammerslag | |
| 2008/0066272 A1 | 3/2008 | Hammerslag | |
| 2008/0066345 A1 | 3/2008 | Hammerslag | |
| 2008/0066346 A1 | 3/2008 | Hammerslag | |
| 2008/0083135 A1 | 4/2008 | Hammerslag | |
| 2011/0196276 A1 | 8/2011 | Kuhn | |
| 2013/0204172 A1 | 8/2013 | Viehweg | |
| 2013/0289463 A1 * | 10/2013 | Watts | A61F 5/0111 602/27 |
| 2013/0310724 A1 | 11/2013 | Kazlow et al. | |
| 2014/0066829 A1 | 3/2014 | Drillio | |
| 2014/0213953 A1 * | 7/2014 | Heyd | A61F 5/0111 602/27 |
| 2014/0276316 A1 | 9/2014 | Bradshaw | |
| 2019/0029863 A1 | 1/2019 | Madden et al. | |

OTHER PUBLICATIONS

International Search Report and Written Opinion dated Apr. 29, 2015 in PCT/US15/014134.

* cited by examiner

RIGID ANKLE SUPPORT SYSTEM

CROSS-REFERENCE TO RELATED APPLICATIONS

This application claims the benefit under 35 U.S.C. § 120 as a continuation of U.S. application Ser. No. 14/612,136, filed on Feb. 2, 2015, now U.S. Pat. No. 10,092,439, which claims the benefit of U.S. Provisional Application No. 61/935,755, filed on Feb. 4, 2014 and U.S. Provisional Application No. 61/935,756, filed Feb. 4, 2014, each of which is hereby incorporated by reference in its entirety.

BACKGROUND

Field

This disclosure relates to a rigid ankle support system and method of making the same.

Description

It is often necessary to form products into custom shapes and fits. One area in which this is particularly relevant is in the use of protective and musculoskeletal supportive devices such as those used in the medical orthopedic field, sports medicine field, protective body gear field, or veterinary field, among other fields. These devices need to provide varied degrees of support and protection yet fit the body closely and comfortably. Items such as form fitting orthopedic casts, orthopedic braces, support devices used in sports medicine, immobilization and alignment devices used for radiation therapy, and supportive devices used in veterinary medicine, as well as protective body gear and other rigid fitted items can all benefit from improved construction techniques and materials.

Orthopedic casts and braces are typically formed on the body by wrapping a fiberglass strip impregnated with soft resin which is activated and hardened by water. They can also be formed from plaster and fabric layers which are activated by water. Polycaprolactone material, such as Orthoplast®, distributed by BSN Medical is also used for braces. This casting and splinting material is heated with hot water to the highest temperature comfortable on the skin, about 160 degrees Fahrenheit. These materials allow the cast or brace to be formed and made in situ about the patient's body part over layers of padding and stockinette. These prior materials have a limited amount of time that they are sufficiently heated to a temperature where 1) they are sufficiently malleable to be formed about the body and 2) the material does not burn the patient or practitioner.

Often casts, splints, braces and other products are required to be formed in complex shapes which are difficult to custom form and fit to a particular user. They are often formed in pieces and attached to the splint or cast body which creates a weaker support. The fit is not always particularly comfortable which leads to compliance issues. Other body injuries may require relatively complex shapes which are difficult and expensive to achieve.

Braces in particular are difficult to form into custom shapes. Braces often need to be flexible in order to allow flexing of the body parts, such as knees, ankles, wrists and other movable body parts. At the same time, the brace needs to be rigid to prevent injury to a weakened body part. Thus, most prior braces are complex mechanical devices that are difficult to create and even more difficult to custom fit to the body.

Orthopedic products such as casts, splints, braces and protective gear, as well as other products are not only difficult to form into complex shapes with conventional materials; they often do not fit the patient particularly well. Since these products are typically manufactured with mechanical mechanisms or attached together with connections such as hook and loop or adhesives, or are non-moldable, they are not able to be custom formed to the patient. This lack of custom fitting leads to discomfort which affects the compliance, use and effectiveness of the product.

SUMMARY

Disclosed herein are moldable, rigid ankle braces and methods of making and using the same. In one aspect of the disclosure, a rigid stabilizing ankle brace is provided. The brace advantageously includes a heat-moldable multi-layer housing having an opening for receiving a user's ankle. Also provided is a footplate removably attached to the housing. The rigid ankle brace further includes a closure mechanism.

The closure mechanism may include at least one tightening strap that is anchorable to the housing and actuatable to tighten the brace about the ankle from a loose state to a tightened state. Optionally, the closure mechanism includes a cable reel elements such as the cable reel attachment systems distributed by BOA Technology Inc. Optionally, the closure mechanism is positioned medially about the housing.

In another aspect, the brace includes a multi-layer housing having an outer layer. The outer layer may be constructed of a fabric such as a knit nylon spandex blend, knit polyester spandex blend, fabrics of nylon, polyester, lycra, or rubberized materials.

Also provided in the multi-layer housing is a middle layer, wherein said middle layer is substantially stiff at a temperature below about 130° F. and moldable at temperatures between about 130° F. and 220° F. In some embodiments, the middle layer is moldable at temperatures between about 130° F. and 275° F.

In yet another aspect, the multi-layer housing includes an inner layer. The inner layer may be constructed of a closed cell foam layer, an open cell foam layer, a gel layer, a soft polymer layer, an insulating fabric, a multilayer or lofted insulating fabric, or combinations thereof Also contemplated is an inner layer having a chemical additive applied. The chemical additive may be an antimicrobial, skin lotion, or other topical therapeutic agent.

In still another aspect, a method of stabilizing an ankle is disclosed. The method includes, for example, providing an ankle brace as described above, heating the ankle brace to a temperature of between about 130° F. to about 275° F., and donning the heated ankle brace to the ankle of a patient in need thereof. The orientation of the brace is optionally manipulated by a health care provider to align the brace relative to said ankle.

BRIEF DESCRIPTION OF THE DRAWINGS

The accompanying drawings, which are incorporated herein and constitute a part of the specification, illustrate embodiments of the disclosure and, together with the description, serve to explain the objects, advantages, and principles disclosed. In the drawings.

DETAILED DESCRIPTION

After reading this description it will become apparent to one skilled in the art how to implement the principles of this disclosure in various alternative embodiments and alternative applications. All possible embodiments of the present disclosure, however, will not be described in detail herein. It is understood that the embodiments presented herein are presented by way of example only. As such, this detailed description of various alternative embodiments should not be construed to limit the scope or breadth of the present disclosure as set forth below.

Disclosed in the present application are a system for orthopedic bracing and a method of the manufacture thereof. A brace is a device used to assist or restrict body movement. As used herein, the terms brace and support may be used interchangeably. An orthosis is an external orthopedic appliance used to support, assist, align, prevent, or correct a deformity or improve function of a movable part of the body. The disclosed bracing system is based, in part, on the surprising and unexpected finding that a brace formed in part of a low temperature, high modulus construction material may provide a quick and custom ankle brace. It is a boon to orthopedic brace construction at least because this innovative brace reduces the number of visits needed for an individual in need thereof to obtain a custom ankle orthosis. The ankle brace as described herein can be fitted in as little as one office visit, thereby reducing the costs to patients, physicians, and healthcare systems. Additionally, the ankle brace provides quick relief and comfort to the patient.

Figure 1:
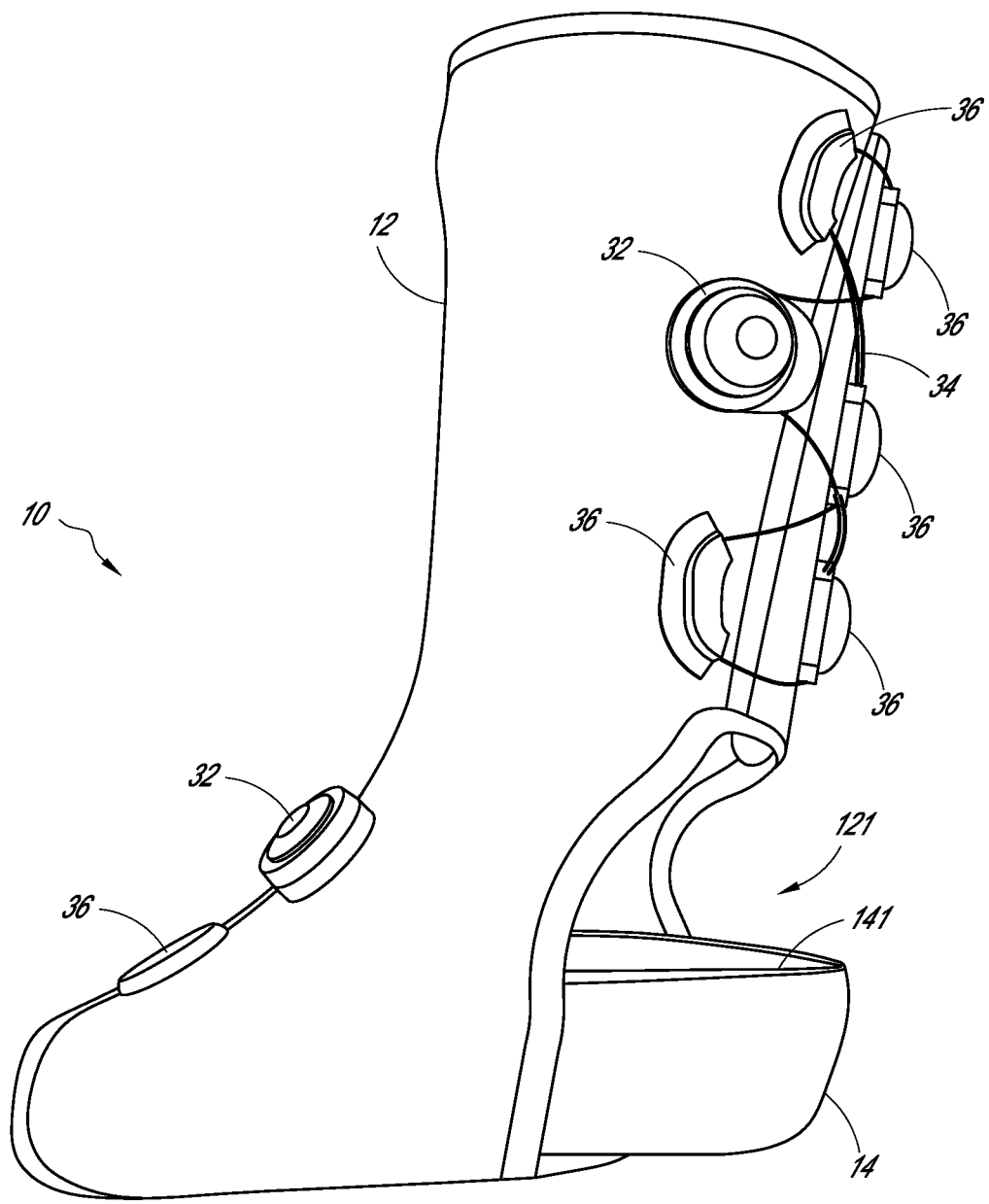
FIG. 1 depicts a lateral (outside) view of an embodiment of an ankle brace according to the present disclosure.

FIG. 1 depicts a lateral (outside) view of an embodiment of an ankle brace according to the present disclosure. As shown, the ankle brace 10 includes a housing 12 configured in size and shape to surround at least a portion of a user's lower leg, including a portion of the foot, a portion of the ankle, and a portion of a calf/shin of the user (not shown). As will be described in greater detail below, the housing 12 may be made from a multi-layer or a single-layer construction configured to allow the housing 12 to be moldable upon heating thereby allowing for the housing 12 to be custom molded to the specific musculoskeletal shape of the patient in order to provide a custom and comfortable fit. When the brace is cooled, housing 12 hardens to provide a rigid support which may immobilize and provide support for a user's ankle.

As shown in the embodiment of FIG. 1, housing 12 of ankle brace 10 may be configured with an open portion 121 allowing access to a heel portion of the user's foot. Open portion 121 allows for increased airflow and comfort while using the ankle brace 10 and may also provide an advantageous view of a patient's foot, for example, by allowing for a visual inspection for discoloration or bruising. Similarly, a proximal end of the ankle brace 10 includes an opening configured to allow a portion of user's leg to extend there through. In some embodiments, a distal end of the ankle brace 10 is also open and configured to allow an end portion of a user's foot (including the toes) to extend there through. In some embodiments, however, open portion 121 for the heel and/or the distal end opening may be omitted.

Ankle brace 10 further may include a footplate 14 configured to support at least a portion of a user's foot. Footplate 14 may include a heel portion 141 configured to receive the heel of a user of the ankle brace 10. In some embodiments, the footplate 14 may be configured to support only a portion of a user's foot. For example, in some embodiments, footplate 14 may be configured to support only a user's heel and may not extend under a front portion (toe end) of a user's foot. In another embodiment, the footplate 14 may support an entire foot of the patient, extending from heel to toe. The specific construction and shape of the footplate 14 will be discussed in greater detail below.

As shown in the embodiment of FIG. 1, the housing 12 can be configured to surround at least a portion of the footplate 14. As shown, the housing 12 rests within a lower portion of the housing 14. In some embodiments, the footplate 14 may be fixedly attached to the housing; however, in other embodiments, the footplate 14 may be removably attached to the housing, for example by Velcro. In some embodiments, housing 12 may not surround footplate 14. For example, in some embodiments, lateral sides of housing 12 connect to lateral sides of footplate 14, and accordingly, no portion of housing 12 extends below the footplate 14. In some embodiments, lateral sides of the housing 12 and lateral sides of the footplate 14 include a coextensive surface along a bottom portion of the ankle brace 10.

In some embodiments, ankle brace 10 may be configured for use without footplate 14, for example, by using housing 12 alone to support and brace a user's ankle. This may be possible because of the heat moldable multi-layer construction of housing 12, which is configured to allow molding to a custom shape. In embodiments of ankle brace 10 that do not include footplate 14, the housing 12 may be molded to provide support to a user's foot, as well as to provide support to a user's ankle and leg.

As will be discussed in greater detail below, the housing 12 may be configured with one or more selectively openable openings (not shown in FIG. 1) which may facilitate donning and doffing ankle brace 10. In some embodiments, the one or more openings may be located on a posterior or anterior portion of ankle brace 10. However, it will be appreciated that other locations for the openings are possible, for example, lateral or medial openings.

Moreover, ankle brace 10 may include one or more closure mechanisms, each of which may comprise a plurality of closure elements, which allow the housing 12 of ankle brace 10 to be tightened around a user's ankle. In some embodiments, the closure mechanisms may further be used to selectively close the one or more selectively openable openings used to facilitate the donning and doffing of ankle brace 10.

In the embodiment of FIG. 1, various closure elements can be seen disposed on housing 12, including cable reel mechanisms 32, lace guides 36, and lace 34. These elements may be considered a tightening strap for the ankle brace 10 and the operation thereof, will be discussed more fully below. In some embodiments, a single closure mechanism controls the tightening of the entire brace, for example by tightening a lace that runs around the entire brace. In other embodiments, more than one closure mechanisms are disposed at various locations on the boot, each mechanism being independently adjustable to provide for localized tightening control.

In some embodiments, the housing 12 and/or footplate 14 may be configured with low profile trims so that ankle brace 10 may be worn under most shoes.

Figure 2:
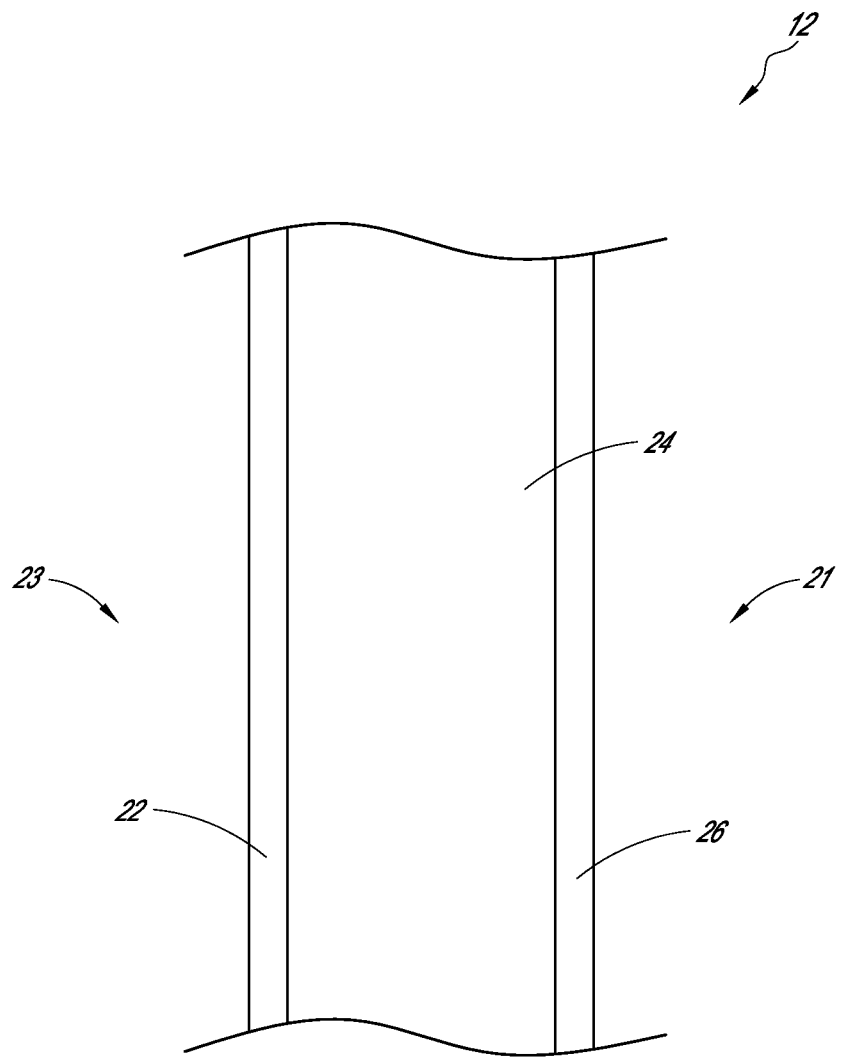
FIG. 2 depicts a cross-sectional view of a portion of the housing in some embodiments and illustrates an example multi-layered construction thereof.

FIG. 2 depicts a cross-sectional view of a portion of the housing 12 in some embodiments of ankle brace 10 and illustrates an example multi-layered construction thereof. The multi-layered construction of the housing 12 includes an outside layer 22, configured to face an outside side 23 (away from the body) of the ankle brace 10. The outside layer 22 is constructed of a relatively stretchy fabric. Preferably the material will easily stretch and possess high strength and durability characteristics. The material may comprise one of the following fabrics: knit nylon spandex blend, knit polyester spandex blend, fabrics of nylon, polyester or other fibers that stretch due to the design of the knit, lycra, rubberized materials, or any other suitable fabric or material. In some embodiments, the material may include a blend of nylon or polyester with spandex (spandex is the generic term for a highly elastic synthetic fiber). In some embodiments, the outer layer 22 is constructed of lycra fabric.

Advantageously, the outer layer 22 provides insulation from heat so that the ankle brace 10 can be handled upon removal from a heating treatment and has enough stretch to form to various shapes encountered in the human ankle (as will be more fully described below). The outer layer 22 may also be made of a stiff foam to provide additional support, as well as environmental protection and/or aesthetics.

When comparing outer layer 22 with the outer surface of a typical plaster or fiberglass brace, it should be noted that outer layer 22, as described above, provides significant improvements in comfort, aesthetics, durability and ease of use.

Additionally, in some embodiments, a fabric, synthetic leather, or other cosmetic covering may be laminated to the outside of the outer layer 22 for purposes of aesthetics or durability. In some embodiments, the fabric known as unbroken loop can be applied at some locations of the ankle brace 10 which has a surface compatible with common hook and loop fasteners such as Velcro™. This may allow closures, extra supports, multipart braces and other devices to be instantly connected using common hook strip fasteners.

The middle layer 24 is the main construct of the housing 12 and is made from a low temperature, high modulus composite material which comprises a percentage of carbon fiber reinforcements added to a polyester PET base plastic. In some embodiments, the middle layer 24 is made from a composite material comprising an 80% polyester PET base reinforced with 20% carbon fiber. In other embodiments, the ratio and/or type of reinforcing material added to the base may be varied. For example, in some embodiments the composite material may comprise 10% carbon fiber and 3% glass as the reinforcing material. In some embodiments, the composite may comprise between 1% and 40% carbon fiber. In some embodiments the composite material may include 10% carbon fiber alone. In some embodiments, the composite material may comprise 5% carbon fiber.

The low temperature, high modulus material of middle layer 24 may be a reinforced thermoplastic polymer material that is easily formable/moldable at relatively low temperatures. For example, in certain embodiments, the material is moldable in a low temperature range that is preferably between about 130° F. to about 220° F. In some embodiments, the material is moldable in a low temperature range that is preferably between about 130° F. and 275° F. Further, the material of the middle layer 24 is stiff at temperatures below approximately 130° F. Accordingly, in some embodiments, the middle layer 24 is heat formable after heating to between about 130° F. and about 275° F. so that it can be fit in real time to the patient and then stiffen as it cools for a patient-specific fit. Again, this process will be described in greater detail below.

Examples of suitable materials for the thermo-formable base polymer of the middle layer 24 include, without limitation, thermoplastic alloys formed from one or more polymers. Suitable polymers include polyester, polyethylene, polyvinyl chloride, polyethylene tetraphthalate, polyamide, or PVC foam such as Sintra™ or Komatex™ or combinations thereof. An example of a suitable heat-formable material includes the thermo-formable material provided by DJO Global under the trademark "Exos 40BX."

In certain embodiments, the modulus of the composite material of the middle layer 24 will exceed the modulus of the base material by at least twice. In other words, the middle layer 24 may be made from a composite material, comprising a base material and a reinforcing material, and the composite material may be configured so that its modulus is at least twice that of the base material alone.

The inner layer 26 of the housing 12 is constructed from a material that provides both comfort and hygiene to the wearer of the ankle brace 10. The inner layer 26 faces the inner side 21 of the ankle brace and interfaces directly with the body of a user. In one embodiment, the inner layer 26 is constructed of foam. In another embodiment, the inner layer 26 is constructed from fabric. In yet another embodiment, the inner layer 26 is constructed from a combination of foam and fabric. The inner layer 26 can also, in some embodiments, be manufactured from materials such as closed cell foam, open cell foam, gel or soft polymer, insulating fabric, multilayer or lofted insulating fabric, or any other cushioned insulative material.

In some embodiments, the inner layer 26 is compressible to comfortably fit closely around a body part of a user. The inner layer 26 also provides cushioning to increase the comfort and compliance of use. The inner layer 26 can comprise a closed cell construction to allow the ankle brace to be waterproof, or it can comprise an open cell construction to provide increased breathability if waterproof features are not desired. This layer can also be a foam formulation configured to accept and dispense therapeutic chemical additives such as antimicrobials, skin lotions, or other medicines and chemicals. In some embodiments, visco-elastic memory foam can be used for this layer to conform precisely to the patient's body.

The multi-layer construction may include holes perforated through the three layers to form holes in various amounts and shapes to provide ventilation, forming features, access to wounds or access to catheters etc. These apertures also allow the middle layer 24 to expand and shrink as necessary as the brace is being molded to the body part. The brace may also be perforated to accept various closure system attachments. In some embodiments, the housing 12 is wrapped once around the extremity and overlapped to some degree. This is to accommodate the varied body diameters and shapes encountered within each sized product and is a feature not found with typical plaster and fiberglass braces. The overlap is also the spot where the closure devices will be placed that allow the brace to be opened or closed in circumference during use. The overlapping ends may thus form an openable opening that allows a user to don and doff the ankle brace 10.

In some embodiments, footplate 14 may also comprise the multi-layered construction described above.

This multi-layered construction for the ankle brace 10 enables the brace to be formed and custom shaped about a body part by heating the product at a relatively low temperature, placing the heated product about the body part, and applying pressure to custom form the product. The process for conforming or molding an ankle brace 10 to the specific and unique musculoskeletal shape of a patient will now be described in detail.

As an initial step, an ankle brace 10 having a general shape is provided. The general shape may be preconfigured to fit generally around the lower leg and ankle of a patient. In some embodiments, the general shape is configured as a one-size-fits-all shape that can be molded, according the method described herein to fit a particular patient. In some embodiments, a patient or a healthcare provider may select an ankle brace 10 having a general shape from among a limited number of size options. For example, in some embodiments, ankle braces 10 may be provided in a first size with a general shape configured to fit adults and a second size with a general shape configured to fit children. In some embodiments, a user or healthcare provider may select a housing 12 with one size and a footplate 14 with a different size, so as to provide increased customization. It should be noted, however, that in some embodiments, only a single size is provided which can be conformed to fit most any patient. The ankle brace 10 provided in the first step is made according to the multi-layer construction described above with reference to FIG. 2.

Next, the ankle brace 10 is heated in a heating/warming source to the prescribed temperature, which in some embodiments is between about 130° F. to about 275° F. As the ankle brace 10 is heated, the middle layer 24 becomes pliable and moldable. Once the desired temperature is achieved, the ankle brace 10 can be removed from the heating/warming source.

In some embodiments, the heating/warming device may be configured to be portable. This may allow a healthcare provider to bring the heating/warming device to the patient. This may be advantageous because it may allow for a complete custom fitting in a single home visit. In some embodiments, however, the ankle brace can be heated in any conventional heating source capable of heating to the prescribed temperature, including a conventional home oven. This may allow a user to purchase an ankle brace and then custom fit it at home. In some embodiments, however, it is advantageous to have a healthcare provider custom fit the ankle brace to ensure a proper fitting.

Next, the heated ankle brace 10 is placed on the patient's ankle while a medical professional holds the foot and ankle in the desired alignment. The medical professional can then gently mold the ankle brace to the specific shape of the patient's ankle by applying gentle pressure on the ankle brace.

In some embodiments, the medical professional may apply pressure to the housing 12 with his/her hands in order to mold the housing 12 to the specific shape of the lower leg of the patient. In some embodiments, the various closures (which will be described in greater detail below) may be tightened while the ankle brace 10 remains heated and the pressure of the closures may mold the ankle brace 10 to the contours of a patient's ankle.

As the ankle brace 10 cools, the middle layer 24 hardens in the molded configuration about the ankle, providing a stabilizing ankle support structure that is specific to that ankle.

Advantageously, the ankle brace 10 can be re-heated and re-shaped to adjust the configuration of the orthosis in response to changes in the patient's anatomy such as swelling in the ankle.

Figure 3:
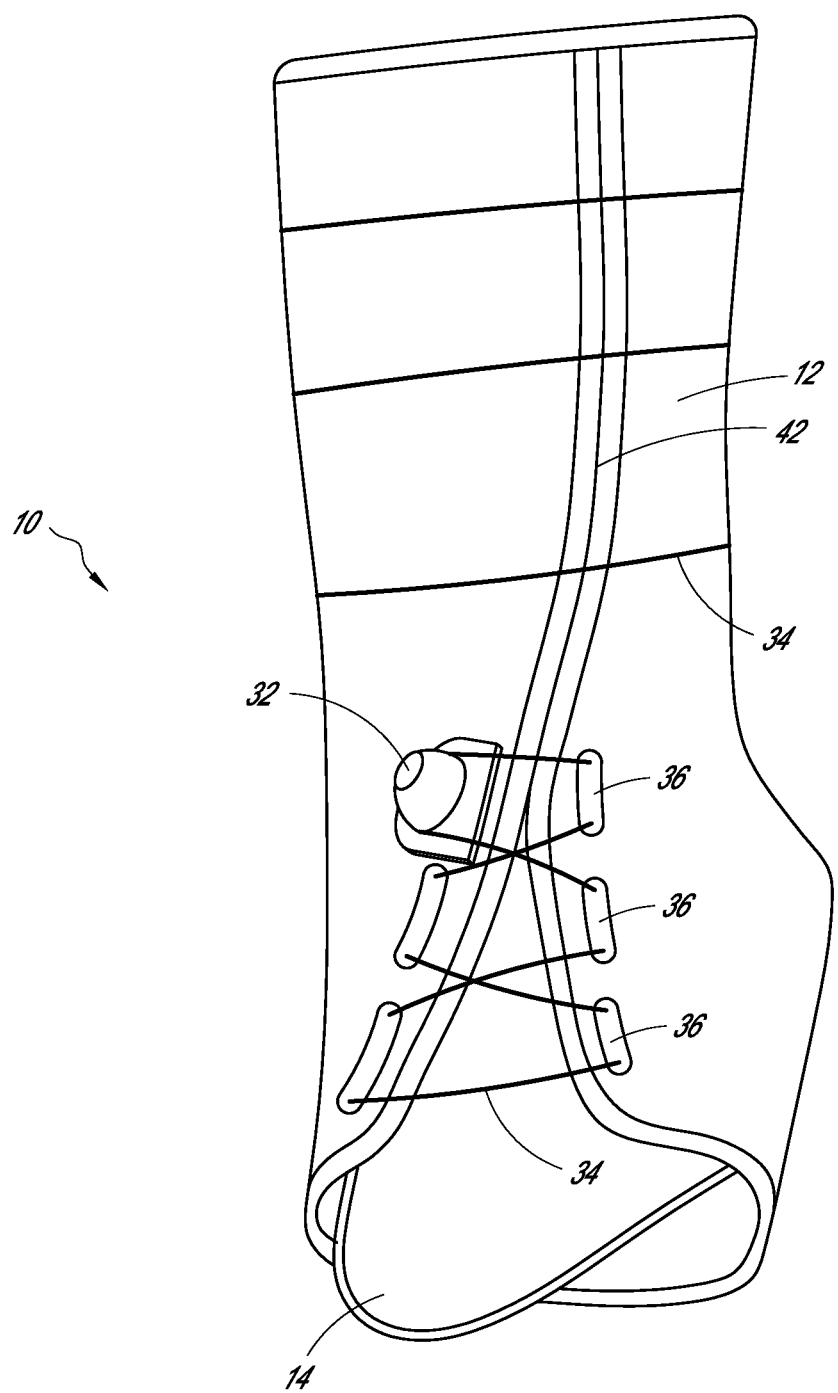
FIG. 3 is an anterior (front) view of an embodiment of an ankle brace.

Specific additional features present in some embodiments of the ankle brace 10 will now be discussed in greater detail with reference to FIGS. 3-5. FIG. 3 is an anterior (front) view of an embodiment of an ankle brace. The ankle brace 10 includes a closure system on the dorsal part of the foot which allows the healthcare professional to modify the width of the brace to accommodate a wide or narrow foot. In some embodiments, the width of the brace may be modified by trimming the width of footplate 14.

In some embodiments, the closure system may comprise a cable reel 32 and a lace 34, where the lace 34 is interwoven through lace supports 36 on each side of the dorsal opening of the brace. The cable reel 32 may then be used to tighten the brace. In other embodiments, the ankle brace 10 may include a traditional tied lace, Velcro, ratchet and latch or other type of closure to tighten the dorsal foot section of the brace. In some embodiments, the dorsal foot section may not include a closure mechanism, for example, in embodiments where the housing uniformly covers the dorsal portion of a foot.

The ankle brace 10 further includes a seam and hot stitch line 42 on the anterior section of the support 10. In preferred embodiments, hot stitching is used to mount the components of the rigid support brace. In other embodiments, the seam 42 might comprise an anterior opening, to accommodate donning the ankle brace 10. In such embodiments, a lace 42 may secure the opening.

Figure 4:
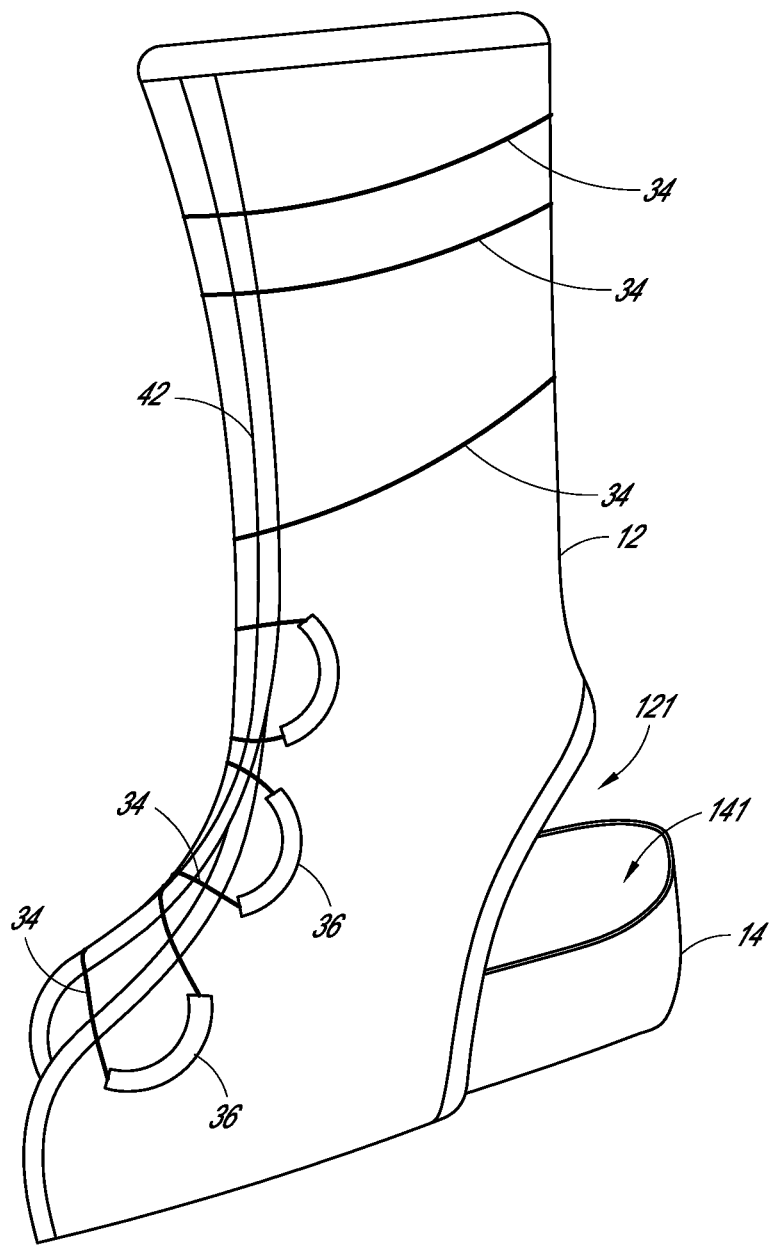
FIG. 4 is a lateral (outside) view of the embodiment of the ankle brace shown in FIG. 3.

FIG. 4 is a lateral view of an ankle brace 10, showing a wraparound lace closure system disposed on the calf portion of the ankle brace, and the mid foot (dorsal) closure system described above. In a preferred embodiment, the ankle brace 10 does not include a hinge. Instead, the brace comprises a modular system wherein the footplate 14 comprises a UCBL style foot orthotic as a base component attached to the housing 12 (which may be configured as an overwrap). The UCBL base footplate 14 is removably attached to the housing 12 and can be worn as a stand-alone footplate device or in combination with the housing 12 for a higher level of support. The UCBL portion provides the healthcare provider with an opportunity to align the hind foot and mid-foot. The housing 12 is preferably wrapped over the footplate 14. The housing 12 serves to stop motion and immobilize the ankle to prevent dorsi-flexion and plantar flexion. The housing 12 further provides a higher level of support.

In some embodiments, the housing 12 may comprise a posterior entry (as discussed below) and one or more closure systems. The posterior entry is adapted to accommodate different widths of the foot while the closure systems are configured to secure the product to the leg, and to allow for various circumferences of the calf. The ankle brace 10 includes at least one fastener, for example an exterior strap or a lace 34. The fastener is anchorable to the housing, for example, by Velcro or by tightening the lace, and is actuatable to tighten the brace about the ankle at the mid-foot region and calf along the over wrap. However, it will be appreciated that any number of closure systems can be utilized to secure and modify the closure of the support brace relative to the patient's body. Securement can be accomplished, for example, using Velcro, buckles, cables, etc. As will be described with reference to FIG. 5, in some embodiments, the closure system includes the use of latches or buckles and cable reel attachment systems which are mounted medially for ease of patient access. Further, a mid-foot closure may allow for greater adjustability of the brace.

Figure 5:
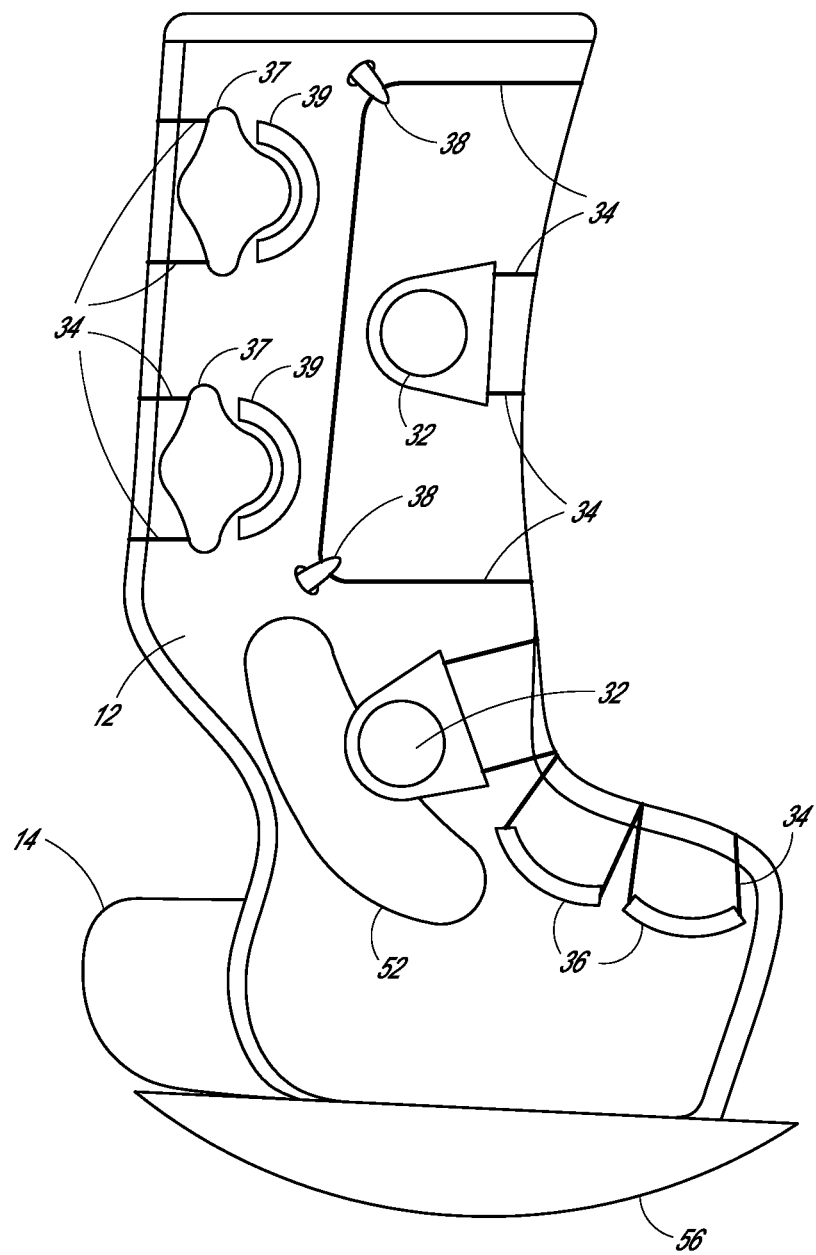
FIG. 5 is a medial (inside) view of one embodiment of an ankle brace.

FIG. 5 illustrates a medial view of an embodiment of an ankle brace 10 with particular attention to one embodiment of the various closure mechanisms that may be employed. A first closure system positioned over the mid foot (dorsally) comprises a cable reel 32, cable line or lace 34, and lace guides 36 as closure components. A second closure system is positioned around the calf/shin portion of the ankle brace 10. It includes a cable reel 32, cable line or lace 34, hooks 38, latches 37 and catches 39. The latches 37 and catches 39 are used to allow posterior entry into the brace and will be discussed in greater detail in reference to FIGS. 6A and 6B. These closure systems provide quick release components to facilitate easy patient access as well as to provide compression of the housing due to the lace 34 encompassing and crossing the entire lower leg. The closure systems can be attached at desired points on the brace. The tension on the lace 34 secures the product to the body. In some embodiments, the closure may include cable reel elements such as the cable reel attachment systems distributed by BOA Technology Inc. and described in U.S. Pat. Nos. 6,289,558; 6,202,953, 5,934,599; and U.S. Patent Applications with Publication Numbers 2008/0083135; 2008/0066346; 2008/0066345; 2008/0066272; 2008/0060168; 2008/0060167; 2006/0156517; 2003/0204938; and 2002/0095750, the contents of each of which is hereby incorporated by reference in its entirety. The cable reel 32 can rotate to tighten the lace 34 and may be pulled vertically (away from the leg) to release the lace 34.

In some embodiments, other fastening mechanisms can be used in place of or in addition to the mechanisms described above, including cord locks, cam cord locks, traditional lacing bows, ratchet lace systems, and other lacing methods. An alternative system using ski boot buckles such as ratchet strip buckles can also be used in a similar fashion with pieces of hook fabric at either end as described in PCT/US2010/025119, the entire contents of which are incorporated herein by reference.

The various adjustable closure mechanisms described herein allow for readjustment of the ankle brace 10 relative to the patient's leg to respond to change of volume swelling. As will be appreciated by a person having skill in the art, the ability to tighten and/or loosen the ankle brace 10 allows for the use of the brace on patient populations who may not otherwise be candidates for wearing a brace. For example, in the case of edema, bracing is contra indicated for a patient. However, with the adjustable closure mechanism, the ankle brace 10 can accommodate a patient dealing with edema. Furthermore, the customized fitting of the ankle brace 10 coupled with the ability to modify the fit of the brace relative to a patient's ankle (to account for swelling, calf width, etc.) facilitates the ease by which a patient may apply and remove the brace.

Also shown in the embodiment of FIG. 5, the ankle brace 10 includes one or more ankle reinforcing members 52. In some embodiments, ankle reinforcing members 52 may be connected to the outside of the housing 12 aligned with the ankle. In some embodiments, ankle reinforcing members 52 may be connected to both the medial and lateral sides, while in some embodiments they are only connected to a single side. The ankle reinforcing member 52 may comprise a shaped structural attachment configured to provide support to an ankle. In some embodiments, the ankle reinforcing member may further restrict the motion of an ankle. Ankle reinforcing member 52 may be made from metal or a rigid plastic. In some embodiments ankle reinforcing member 52 may further be connected to the footplate 14.

In some embodiments, ankle brace 10 may include a rocker sole 56 attached to the bottom of the ankle brace 10. The rocker sole 56 may be permanently or selectively attached. In some embodiments, the rocker sole 56 may include tread, so that the ankle brace 10 can be worn without a shoe. In further embodiments, the rocker sole 56 may comprise a curved shape to aid the user in walking without the movement of the ankle.

Figure 6A:
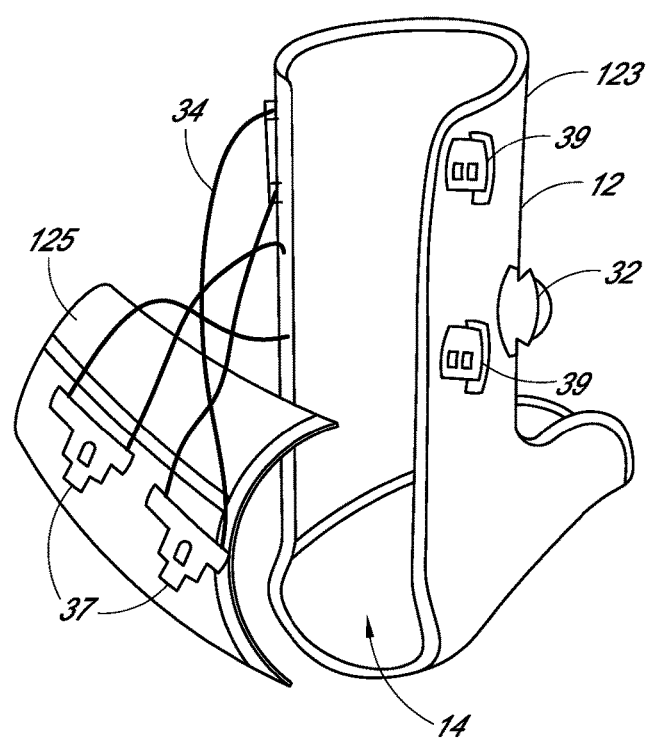
FIG. 6A depicts a posterior view of one embodiment of an ankle brace, showing a removable portion of the housing in a removed position to allow a posterior opening for donning and doffing the brace.
Figure 6B:
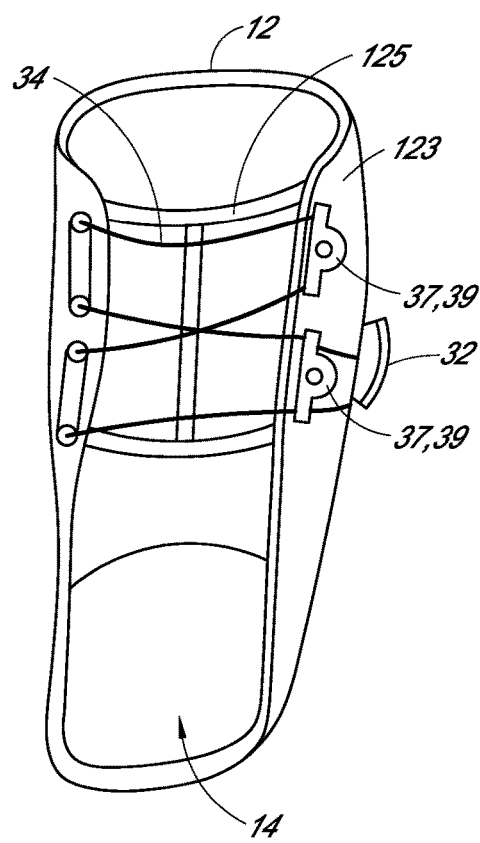
FIG. 6B is a posterior view of the embodiment of an ankle rigid support brace shown in FIG. 6A with a removable portion of the housing shown in place as if the brace were being worn by a user.

FIGS. 6A and 6B are posterior views of an embodiment of ankle brace 10 including a posterior openable opening for donning and doffing the ankle brace 10. FIG. 6A depicts a posterior view of one embodiment of an ankle brace 10, showing a removable portion 125 of the housing 12 in a removed position. FIG. 6B is a posterior view of the embodiment of an ankle rigid support brace shown in FIG. 6A with a removable portion 125 of the housing 12 shown in place as if the brace were being worn by a user. The removable portion 125 is configured to allow a posterior entry to the brace. In some embodiments, the posterior entry allows for the ankle brace 10 to stay in a patient's shoe as donning and doffing is accomplished via the posterior entry.

Certain aspects of the closure system of FIG. 5, including the use of latches 37 and catches 39 can be better understood in reference to FIGS. 6A and 6B. In the illustrated embodiment, closure latches 37 are disposed on the removable rear portion 125. The latches 37 are attached to the lace 34. When the removable rear portion 125 is in place, the latches 37 are attached to corresponding catches 39, which are attached to the front portion of the housing 123. The lace 43 may then be tightened by twisting cable reel 32, thus securing the brace.

The ankle brace can be formed by injection molding using a 3-dimensional mold that accommodates medial-lateral thickness, anterior-posterior width, and preshaped contouring along the medial face, particularly in the ankle region. In alternative embodiments, the brace can be machined, die-cut, or 3D printed.

The ankle brace can be used to treat a plurality of ankle instabilities and indications. Indications may include, without limitation, use for the treatment of Posterior Tibial Tendon Dysfunction (PTTD), ankle arthritis, lateral ankle instability, and treatment of Achilles tendons.

In some embodiments, a rigid stabilizing ankle brace may include a heat-moldable single-layer housing having a selectively openable opening for receiving a user's ankle, and a closure mechanism disposed on the housing. In some embodiments, the single-layer housing may be made from a material that substantially stiff at a temperature below about 130° F. and moldable at temperatures between about 130° F. and 220° F. In some embodiments, the single-layer housing may be made from a material that substantially stiff at a temperature below about 130° F. and moldable at temperatures between about 130° F. and 275° F. The heat-moldable housing may also include a footplate. In some embodiments, the closure mechanism includes at least one tightening strap or lace that is anchorable to the housing and actuatable to tighten the brace about the ankle from a loose state to a tightened state.

In some embodiments these principles may be applied to form braces for other body parts, including, but not limited to, hands, wrists, elbows, shoulders, knees, hips, spine, or neck. While the various figures depicting side views of embodiments of ankle brace 10 have been described as showing either a medial or lateral side of the brace, other embodiments exist which may be represented by the same figures, yet describe the opposite side of the brace. For example, while FIG. 5 has been described as showing a medial side of the brace, the figure may also represent another embodiment, wherein the elements shown are disposed on the lateral side of the brace.

Each reference in the present application is hereby incorporated by reference in its entirety. Further, the above description of disclosed embodiments is provided to enable any person skilled in the art to make or use the invention. Various modifications to the embodiments will be readily apparent to those skilled in the art; the generic principles defined herein can be applied to other embodiments without departing from spirit or scope of the invention. All references cited are hereby incorporated by reference herein in their entireties and made part of this application. The invention is not intended to be limited to the embodiments shown herein but is to be accorded the widest scope consistent with the principles and novel features disclosed herein.

What is claimed is:

1. A rigid stabilizing ankle brace, comprising:
a heat-moldable multi-layer housing having a selectively openable opening disposed posteriorly on the housing, the opening configured to receive a user's foot, wherein each layer of the multi-layer housing is configured to extend from a medial side of the foot around the user's ankle and across the user's shin to a distal side of the foot, and wherein the multilayer housing comprises a removable portion that is separable from a remainder of the multilayer housing;
wherein the opening comprises an open position and a closed position, the open position configured to allow posterior entry of the foot into the ankle brace and the closed position configured to secure the ankle brace to the user's foot, and wherein removing the removable portion places the opening in the open position.

2. The brace of claim 1 further comprising a closure mechanism configured to transition the openable opening between the open position and the closed position.

3. The brace of claim 2, wherein the closure mechanism comprises at least one latch and at least one corresponding catch positioned on one side of the openable opening, the at least one latch and at least one catch configured to transition the openable opening between the open position and the closed position by opening or closing the circumference of the brace around a leg of the user.

4. The brace of claim 3, wherein the closure mechanism comprises a cable reel mechanism configured to tighten the at least one tightening strap or lace by rotating the cable reel mechanism.

5. The brace of claim 4, wherein the cable reel mechanism comprises a quick release feature for quickly loosening the at least one tightening strap or lace.

6. The brace of claim 2, further comprising a second closure mechanism configured to tighten the brace at a location different from the closure mechanism configured to transition the openable opening between the open position and the closed position.

7. The brace of claim 6, wherein the second closure mechanism is configured to be positioned over a dorsal area of the foot.

8. The brace of claim 2, wherein the closure mechanism comprises at least one tightening strap or lace that is anchorable to the housing and actuatable to tighten the brace about the ankle from a loose state to a tightened state.

9. The brace of claim 1, wherein the multilayer housing comprises an open portion configured to receive the user's heel.

10. The brace of claim 9, wherein the brace comprises a footplate configured to extend posteriorly into the open portion of the multilayer housing, the footplate configured to receive the user's heel.

11. The brace of claim 10, wherein the footplate is removable from the multilayer housing.

12. The brace of claim 1, wherein the multi-layer housing comprises at least three layers, each of the three layers configured to extend from a medial side of the foot around the user's ankle and across the user's shin to a distal side of the foot.

13. The brace of claim 12, wherein the multi-layer housing comprises a middle layer which is substantially stiff at a temperature below about 130° F. and moldable at temperatures between about 130° F. and 220° F.

14. The brace of claim 1, wherein the removable portion is retained to the remainder of the multilayer housing on one side of the opening by a tightening strap or lace which is anchored to the one side of the opening.

15. The brace of claim 1, wherein the openable opening is formed by overlapping ends of the multilayer housing.

16. A method of stabilizing an ankle, comprising:
providing a rigid stabilizing ankle brace comprising a heat-moldable multi-layer housing having an opening for receiving a user's ankle and a removable portion that is separable from a remainder of the multilayer housing, the opening being selectively openable between an open position and a closed position, the open position configured to allow posterior entry of the user's foot into the ankle brace and the closed position configured to secure the ankle brace to the user, wherein each layer of the multi-layer housing is configured to extend from a medial side of the foot around the user's ankle and across the user's shin to a distal side of the foot, wherein removing the removable portion places the opening in the open position;
heating the housing to between about 130° F. to about 275° F.; and
donning the heated housing to the ankle of a patient in need thereof.

17. The method of claim 16, wherein the multi-layer housing comprises a middle layer, wherein the middle layer is substantially stiff at a temperature below about 130° F. and moldable at temperatures between about 130° F. and 275° F.

18. The method of claim 16, further comprising applying pressure to the heated housing to mold the housing to conform to a specific shape of a leg of the user, wherein applying pressure comprises tightening a first strap or lace disposed on a leg portion of the brace and tightening a second strap or lace disposed on a foot portion of the brace while the housing is heated.

19. The method of claim 16, wherein donning the heated housing to the ankle of a patient comprises attaching a footplate to the heated housing.

* * * * *